(12) United States Patent
Webb

(10) Patent No.: US 7,205,400 B2
(45) Date of Patent: Apr. 17, 2007

(54) ARRAY FABRICATION

(75) Inventor: Peter G. Webb, Menlo Park, CA (US)

(73) Assignee: Agilent Technologies, Inc., Santa Clara, CA (US)

( * ) Notice: Subject to any disclaimer, the term of this patent is extended or adjusted under 35 U.S.C. 154(b) by 331 days.

(21) Appl. No.: 10/649,105

(22) Filed: Aug. 26, 2003

(65) Prior Publication Data

US 2005/0100480 A1    May 12, 2005

Related U.S. Application Data

(62) Division of application No. 09/629,500, filed on Jul. 31, 2000, now Pat. No. 6,613,893.

(51) Int. Cl.
*C07H 21/00* (2006.01)
*G06F 19/00* (2006.01)

(52) U.S. Cl. .................. 536/25.3; 702/19; 702/20

(58) Field of Classification Search ............ None
See application file for complete search history.

(56) References Cited

U.S. PATENT DOCUMENTS

| | | | |
|---|---|---|---|
| 4,877,745 A | 10/1989 | Hayes et al. | |
| 5,449,754 A | 9/1995 | Nishioka | |
| 5,508,200 A | 4/1996 | Tiffany et al. | |
| 5,624,484 A * | 4/1997 | Takahashi et al. | 106/31.75 |
| 5,658,802 A | 8/1997 | Hayes et al. | |
| 5,733,729 A * | 3/1998 | Lipshutz et al. | 435/6 |
| 5,807,522 A | 9/1998 | Brown et al. | |
| 6,001,309 A | 12/1999 | Gamble et al. | |
| 6,024,925 A | 2/2000 | Little et al. | |
| 6,028,189 A * | 2/2000 | Blanchard | 536/25.3 |
| 6,453,241 B1 | 9/2002 | Bassett et al. | |

FOREIGN PATENT DOCUMENTS

| | | |
|---|---|---|
| EP | 0 469 444 | 2/1992 |
| WO | WO 94/27719 | 12/1994 |
| WO | WO 95/25116 | 9/1995 |
| WO | WO 98/41531 | 9/1998 |
| WO | WO 99/22867 | 5/1999 |
| WO | WO 9922867 A1 * | 5/1999 |
| WO | WO 00/39338 | 7/2000 |

OTHER PUBLICATIONS

A.P. Blanchard et al., "High-Density Oligonucleotide Arrays", Biosenser & Bioelectronics, vol. 11, No. 6/7, Apr. 26, 1996, pp. 687-690.

Xiao-Dong Sun et al., "Solution-Phase Synthesis of Luminescent Materials Libraries", Advanced Materials, vol. 9, No. 13, 1997, pp. 1046-1049.

European Patent Office Communication dated Jan. 2, 2003, European Search Report for EP 01 30 6574, (corresponding to U.S. Appl. No. 09/629,500) dated Dec. 19, 2002, and Annex to the European Searvh Report.

* cited by examiner

*Primary Examiner*—Young J. Kim

(57) ABSTRACT

A method, apparatus, and computer program, for fabricating multiple arrays arranged successively in a first direction on a substrate and each having multiple feature sets arranged successively in the first direction within the array. The method uses a head system having multiple successive sets of dispensers. In the method, the head system is advanced in the first direction over the substrate while dispensing drop sets for each array from dispenser sets so as to form the arrays. In one aspect, drop sets are dispensed in an order the reverse of that from which the dispenser sets pass over a given location on the substrate as the head system advances in the first direction. In this case, each dispenser set deposits a drop set at a distance ahead of a drop set deposited by a preceding dispenser set which is less than the distance to the successive drop dispenser set which deposits the next drop set.

14 Claims, 9 Drawing Sheets

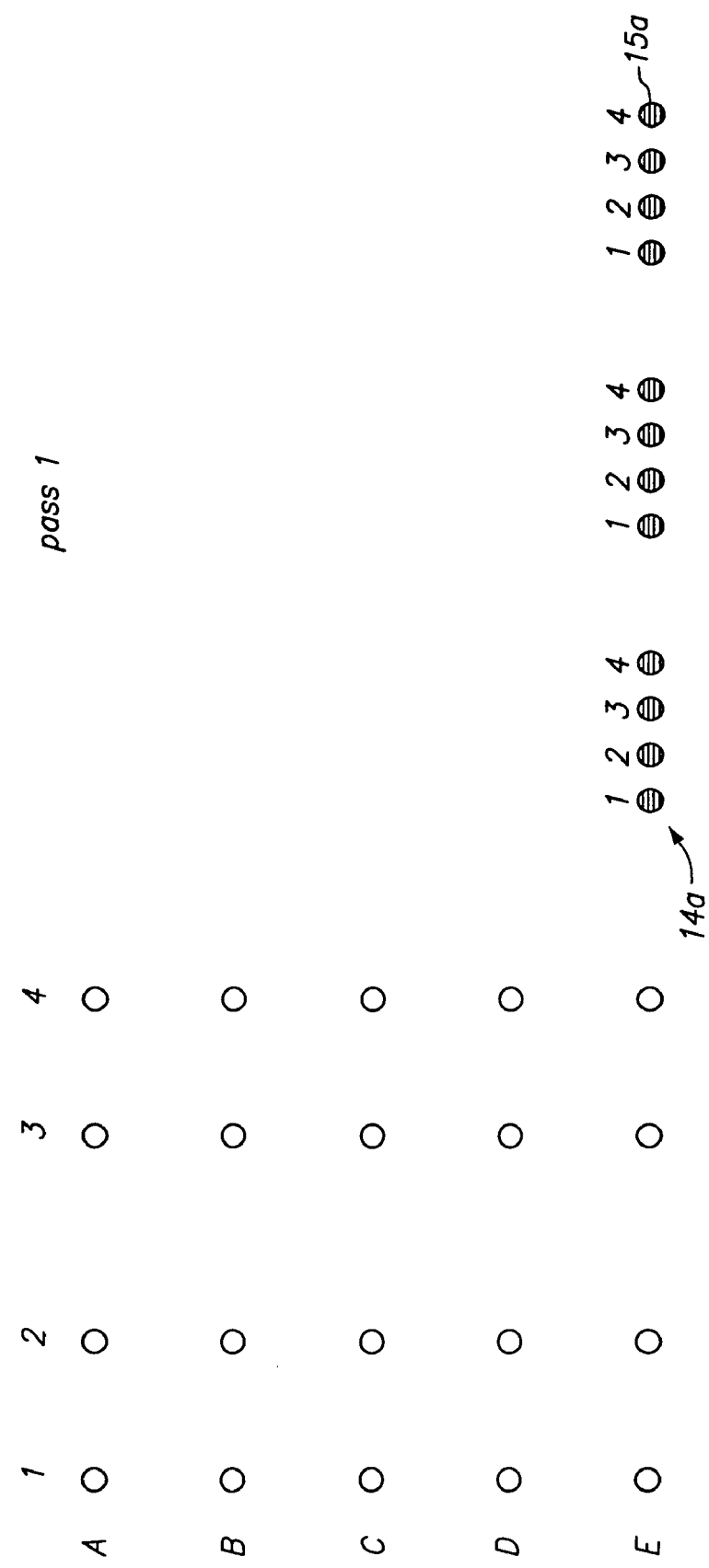

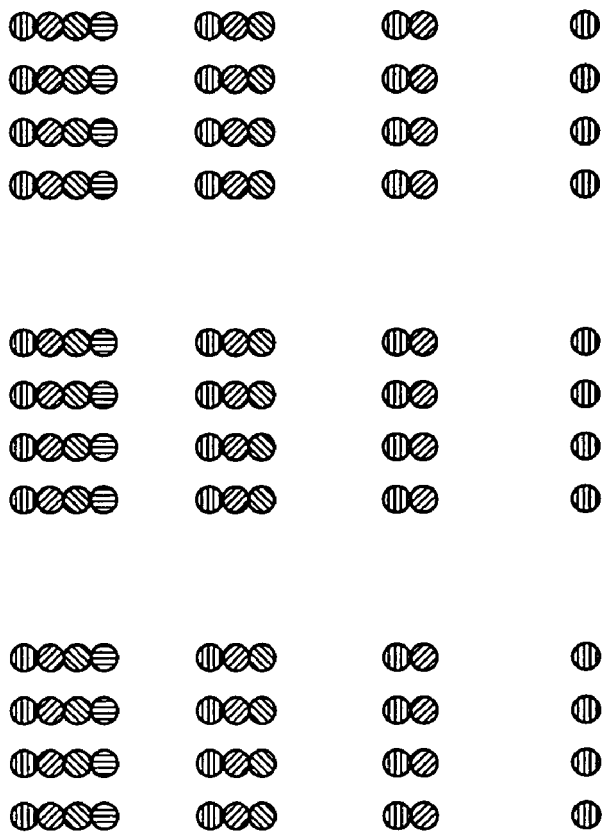

|   | 1 | 2 | 3 | 4 |
|---|---|---|---|---|
| A | O | O | O | O |
| B | O | O | O | O |
| C | O | O | O | O |
| D | O | O | O | O |
| E | O | O | O | O | pass 5 pass 6

FIG. 4G

ARRAY FABRICATION

CROSS REFERENCE TO RELATED APPLICATIONS

This application is a divisional application of U.S. patent application Ser. No. 09/629,500 filed Jul. 31, 2000, now U.S. Pat. No. 6,613,893, from which priority is claimed under 35 U.S.C. 120 and which is incorporated herein by reference.

FIELD OF THE INVENTION

This invention relates to arrays, particularly polynucleotide arrays such as DNA arrays, which are useful in diagnostic, screening, gene expression analysis, and other applications.

BACKGROUND OF THE INVENTION

Polynucleotide arrays (such as DNA or RNA arrays), are known and are used, for example, as diagnostic or screening tools. Such arrays include regions of usually different sequence polynucleotides arranged in a predetermined configuration on a substrate. These regions (sometimes referenced as "features") are positioned at respective locations ("addresses") on the substrate. The arrays, when exposed to a sample, will exhibit an observed binding pattern. This binding pattern can be detected upon interrogating the array. For example all polynucleotide targets (for example, DNA) in the sample can be labeled with a suitable label (such as a fluorescent compound), and the fluorescence pattern on the array accurately observed following exposure to the sample. Assuming that the different sequence polynucleotides were correctly deposited in accordance with the predetermined configuration, then the observed binding pattern will be indicative of the presence and/or concentration of one or more polynucleotide components of the sample.

Biopolymer arrays can be fabricated by depositing previously obtained biopolymers (such as from synthesis or natural sources) onto a substrate, or by in situ synthesis methods. Methods of depositing obtained biopolymers include dispensing droplets to a substrate from dispensers such as pin or capillaries (such as described in U.S. Pat. No. 5,807,522) or such as pulse jets (such as a piezoelectric inkjet head, as described in PCT publications WO 95/25116 and WO 98/41531, and elsewhere). For in situ fabrication methods, multiple different reagent droplets are deposited from drop dispensers at a given target location in order to form the final feature (hence a probe of the feature is synthesized on the array stubstrate). The in situ fabrication methods include those described in U.S. Pat. No. 5,449,754 for synthesizing peptide arrays, and described in WO 98/41531 and the references cited therein for polynucleotides. The in situ method for fabricating a polynucleotide array typically follows, at each of the multiple different addresses at which features are to be formed, the same conventional iterative sequence used in forming polynucleotides from nucleoside reagents on a support by means of known chemistry. This iterative sequence is as follows: (a) coupling a selected nucleoside through a phosphite linkage to a functionalized support in the first iteration, or a nucleoside bound to the substrate (i.e. the nucleoside-modified substrate) in subsequent iterations; (b) optionally, but preferably, blocking unreacted hydroxyl groups on the substrate bound nucleoside; (c) oxidizing the phosphite linkage of step (a) to form a phosphate linkage; and (d) removing the protecting group ("deprotection") from the now substrate bound nucleoside coupled in step (a), to generate a reactive site for the next cycle of these steps. The functionalized support (in the first cycle) or deprotected coupled nucleoside (in subsequent cycles) provides a substrate bound moiety with a linking group for forming the phosphite linkage with a next nucleoside to be coupled in step (a). Final deprotection of nucleoside bases can be accomplished using alkaline conditions such as ammonium hydroxide, in a known manner.

The foregoing chemistry of the synthesis of polynucleotides is described in detail, for example, in Caruthers, *Science* 230: 281–285, 1985; Itakura et al., *Ann. Rev. Biochem.* 53: 323–356; Hunkapillar et al., *Nature* 310: 105–110, 1984; and in "Synthesis of Oligonucleotide Derivatives in Design and Targeted Reaction of Oligonucleotide Derivatives", CRC Press, Boca Raton, Fla., pages 100 et seq., U.S. Pat. No. 4,458,066, U.S. Pat. No. 4,500,707, U.S. Pat. No. 5,153,319, U.S. Pat. No. 5,869,643, EP 0294196, and elsewhere In array fabrication, the quantities of polynucleotide available, whether by deposition of previously obtained polynucleotides or by in situ synthesis, are usually very small and expensive. Additionally, sample quantities available for testing are usually also very small and it is therefore desirable to simultaneously test the same sample against a large number of different probes on an array. These conditions require use of arrays with large numbers of very small, closely spaced features. It is important in such arrays that features actually be present, that they are put down accurately in the desired target pattern, are of the correct size, and that the DNA is uniformly coated within the feature. Failure to meet such quality requirements can have serious consequences to diagnostic, screening, gene expression analysis or other purposes for which the array is being used.

However, in order to make arrays at a reasonable cost per array, it is also important that large numbers of arrays be fabricated in a short time. When drops are dispensed to form the arrays, this typically involves dispensing drops from a number of dispensers in co-ordination with scanning the dispensers in some pattern over a substrate (with one or more dispenser re-loadings, as desired). For example, drops for a portion of each array can be dispensed, the dispensers relocated, drops for the same portion of another array dispensed, and the process repeated followed by re-loading of the dispensers and repeating the foregoing sequence for another portion of all the arrays. However, such a pattern requires a large number of movements and hence a relatively long time to complete.

It would be desirable then, to provide a means for fabricating multiple arrays on a substrate while keeping the movement pattern of the multiple dispensers relatively simple.

SUMMARY OF THE INVENTION

The present invention provides in one aspect, a method of fabricating multiple arrays arranged successively in a first direction on a substrate. Each such array has multiple feature sets within the array which are also arranged successively in the first direction. The method uses a head system is used which has multiple successive sets of dispensers (for example, pulse jets such as piezoelectric or thermoelectric jets). In the method, the head system is advanced in the first direction over the substrate. Drop sets are dispensed from successive dispenser sets for each array in co-ordination with such movement, such that each drop set for multiple arrays are dispensed for each array.

In one aspect of the method, drop sets are dispensed from dispenser sets in an order the reverse of that from which the dispenser sets pass over a given location on the substrate as the head system advances in the first direction. In this aspect, each dispenser set deposits a drop set at a distance ahead of (as measured in the first direction) a drop set deposited by a preceding dispenser set which is less than the distance to the successive drop dispenser set which deposits the next drop set. Thus, while a given dispenser set is depositing drops for one feature set of an array, the dispenser sets which will deposit drops for successive feature sets of the same array have still not passed over the one feature set position of the same array (that is, they are still "behind" the given dispenser set in relation to the direction of head advancement).

The arrays fabricated may have a distance between adjacent sets of features within the arrays, which is less than the distance between adjacent sets of dispensers. In fact, in one aspect of the present invention, arrays are fabricated by advancing and dispensing from the previously described head system, to obtain arrays with corresponding feature set spacing (for example, first feature set spacing) between adjacent arrays which is less than the total spacing (as measured in the direction of head advancement) of the dispenser sets which formed the arrays. Furthermore, the sets of features may extend in a direction transverse to the first direction. In this case, the method may additionally include moving the head in the transverse direction and dispensing the drop sets in co-ordination with such transverse movement so as to deposit drops along such feature sets.

The "advancing" need not be a continuous motion, and in a particular aspect, the advancing and dispensing step may involve a number of sub-steps. Such sub-steps may include: while the head system is in one position in the first direction, depositing drop sets from at least one, and preferably multiple different dispenser sets for feature sets of different positions within multiple arrays; advancing the head system in the first direction to a next position; and repeating the foregoing two steps for successive feature sets within the arrays. During the repetitions, for each of the successive feature sets within the arrays, a corresponding dispenser set is used which deposited at a same feature set position of a previous array in step the first step during a previous cycle. This procedure may particularly be used in the case where the feature sets extend in a direction transverse to the first direction. In this case the method can additionally include moving the head in the transverse direction during the first step and dispensing the drop sets in co-ordination with such transverse movement so as to deposit drops along such feature sets.

Any desired number of successively arranged arrays can be fabricated on the same substrate by the method, each array having any desired number of features sets (for example, at least three, at least five, at least ten arrays, or at least twenty arrays each with at least three, at least five, at least ten, at least twenty, or at least one hundred feature sets).

The present invention can be applied to fabricating arrays of any chemical moieties, with any number of features within each set of an array being the same or different. The invention may, for example, be applied to fabricating arrays of monomeric moieties or polymers, such as biopolymers. (for example, polynucleotides or peptides). In the case of polymeric moieties, the drop sets may contain the polymeric moieties themselves (such as solutions of the polynucleotides or peptides) or monomeric moieties (such as nucleotides or amino acids) which may be reacted in sequence (through deposition of multiple different monomer containing moieties at each of the feature locations) to form the desired polymeric moieties. Any of the drops within a dispensed set of drops may be of the same or different composition, and any of the features within a feature set of the array may be the same or different composition (with any number of the feature sets being of the same or different composition).

Each feature set of the arrays may have multiple features arranged successively in the first direction. In this case, the dispenser sets may also be arranged successively in the first direction, with each set having multiple dispensers arranged successively within the set in a direction transverse to the first direction. For example, the feature sets may be rows of features arranged successively in the first direction (which implies, in the case of an array, that the individual rows extend lengthwise in a direction transverse to the first direction). The dispenser sets may also be arranged successively in the first direction with each set having multiple dispensers arranged successively within the set in a second direction transverse to the first. For example, the dispenser sets are rows of dispensers, each of which extends lengthwise in the transverse direction.

The present invention further provides an apparatus of the type described above in connection with any of the methods of the present invention. Such an apparatus may include a head system of a type already described above, and a transport system to advance the head system in the first direction with respect to a substrate. A processor communicates with the head system and transport system. The processor can advance the head system in the first direction over the substrate while coordinating drop dispensing from the head system with the advancement. In particular, the processor may dispense drop sets from successive dispenser sets for each array, such that each drop set for multiple arrays is deposited by a corresponding dispenser set which earlier deposited at a same feature set position within a previous array, in a manner as already described. The apparatus may optionally additionally include a loading station with receptacles to retain multiple different fluids such that the dispensers can be simultaneously brought into contact with respective receptacles for loading the dispensers with the different fluids. Each dispenser in such an apparatus may be constructed so that it holds no more than 100 µl of a fluid to be dispensed as drops (or no more than 10 µl or no more than 1 µl of such fluid). By the dispenser holding a certain volume is referenced the entire dispenser including any reservoir in continuous communication with the remainder of the dispenser.

The present invention further provides a computer program for use with an apparatus such as already described above, having a head system-, transport system, and processor. The computer program, when loaded into the processor, performs the steps of a method of the present invention (by controlling the apparatus, particularly the head system and transport system, appropriately). The computer program may be communicated to the processor (for example, from a remote location), or may be stored on a computer program product comprising a computer readable storage medium.

The present invention can allow for the fabrication of multiple arrays on a substrate in a relatively efficient manner with a simple movement pattern for the dispensers.

BRIEF DESCRIPTION OF THE DRAWINGS

Embodiments of the invention will now be described with reference to the drawings, in which.

To facilitate understanding, identical reference numerals have been used, where practical, to designate identical elements that are common to the figures.

DETAILED DESCRIPTION OF EMBODIMENTS OF THE INVENTION

Figure 1:
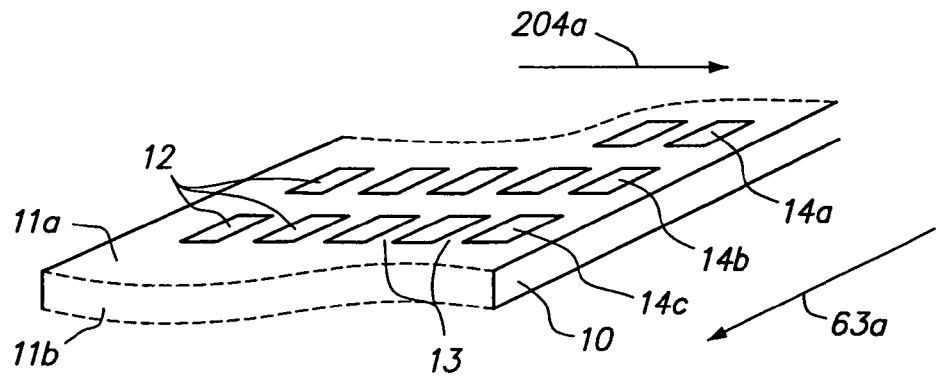
FIG. 1 illustrates a substrate carrying multiple arrays, such as may be fabricated by methods of the present invention.

In the present application, unless a contrary intention appears, the following terms refer to the indicated characteristics. A "biopolymer" is a polymer of one or more types of repeating units. Biopolymers are typically found in biological systems (although they may be made synthetically) and particularly include peptides or polynucleotides, as well as such compounds composed of or containing amino acid analogs or non-amino acid groups, or nucleotide analogs or non-nucleotide groups. This includes polynucleotides in which the conventional backbone has been replaced with a non-naturally occurring or synthetic backbone, and nucleic acids (or synthetic or naturally occurring analogs) in which one or more of the conventional bases has been replaced with a group (natural or synthetic) capable of participating in Watson-Crick type hydrogen bonding interactions. Polynucleotides include single or multiple stranded configurations, where one or more of the strands may or may not be completely aligned with another. A "nucleotide" refers to a sub-unit of a nucleic acid and has a phosphate group, a 5 carbon sugar and a nitrogen containing base, as well as functional analogs (whether synthetic or naturally occurring) of such sub-units which in the polymer form (as a polynucleotide) can hybridize with naturally occurring polynucleotides in a sequence specific manner analogous to that of two naturally occurring polynucleotides. For example, a "biopolymer" includes DNA (including cDNA), RNA, oligonucleotides, and PNA and other polynucleotides as described in U.S. Pat. No. 5,948,902 and references cited therein (all of which are incorporated herein by reference), regardless of the source. An "oligonucleotide" generally refers to a nucleotide multimer of about 10 to 100 nucleotides in length, while a "polynucleotide" includes a nucleotide multimer having any number of nucleotides. A "biomonomer" references a single unit, which can be linked with the same or other biomonomers to form a biopolymer (for example, a single amino acid or nucleotide with two linking groups one or both of which may have removable protecting groups). A "peptide" is used to refer to an amino acid multimer of any length (for example, more than 10, 10 to 100, or more amino acid units). A biomonomer fluid or biopolymer fluid reference a liquid containing either a biomonomer or biopolymer, respectively (typically in solution).

A "set" or "sub-set" of any item (for example, a set of features) may contain one or more than one of the item (for example, a dispenser set may have one or more than one dispensers). An "array", unless a contrary intention appears, includes any one, two or three dimensional arrangement of addressable regions bearing a particular chemical moiety to moieties (for example, biopolymers such as polynucleotide sequences) associated with that region. An array is "addressable" in that it has multiple regions of different moieties (for example, different polynucleotide sequences) such that a region (a "feature" or "spot" of the array) at a particular predetermined location (an "address") on the array will detect a particular target or class of targets (although a feature may incidentally detect non-targets of that feature). Array features are typically, but need not be, separated by intervening spaces. In the case of an array, the "target" will be referenced as a moiety in a mobile phase (typically fluid), to be detected by probes ("target probes") which are bound to the substrate at the various regions. However, either of the "target" or "target probes" may be the one which is to be evaluated by the other (thus, either one could be an unknown mixture of polynucleotides to be evaluated by binding with the other). An "array layout" refers collectively to one or more characteristics of the features, such as feature positioning, one or more feature dimensions, and some indication of a moiety at a given location. "Hybridizing" and "binding", with respect to polynucleotides, are used interchangeably.

When one item is indicated as being "remote" from another, this is referenced that the two items are at least in different buildings, and may be at least one mile, ten miles, or at least one hundred miles apart. "Communicating" information references transmitting the data representing that information as electrical signals over a suitable communication channel (for example, a private or public network). "Forwarding" an item refers to any means of getting that item from one location to the next, whether by physically transporting that item or otherwise (where that is possible) and includes, at least in the case of data, physically transporting a medium carrying the data or communicating the data.

It will also be appreciated that throughout the present application, that words such as "top", "upper", and "lower" are used in a relative sense only. Items (such as arrays) being "successive", "successively arranged" or the like terms, in a given direction, references a those items being disposed in a series one after another in that direction. However, each item of successive items need not necessarily be adjacent or neighboring another such item (although they often will be). For example, a given group of arrays disposed successively in a first direction may have other arrays interposed between them which are not of the referenced group. "Fluid" is used herein to reference a liquid. Reference to a singular item, includes the possibility that there are plural of the same items present. Furthermore, when one thing is "advanced", "moved", "moving", "re-positioned", "scanned", or the like, with respect to another, this implies relative motion only such that either thing or both might actually be moved in relation to the other. For example, when dispensers are "advanced" relative to a substrate, either one of the dispensers or substrate may actually be put into motion by the transport system while the other is held still, or both may be put into motion. All patents and other cited references are incorporated into this application by reference.

Figure 2:
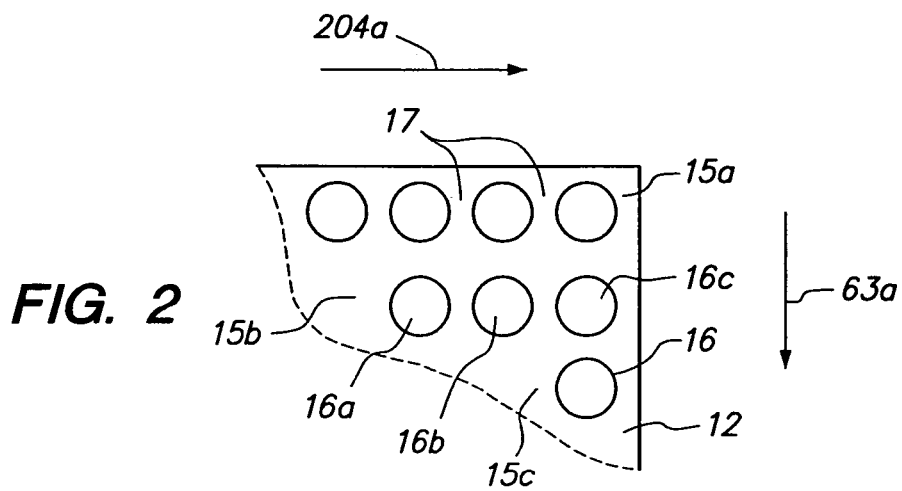
FIG. 2 is an enlarged view of a portion of FIG. 1 showing ideal spots or features.
Figure 3:
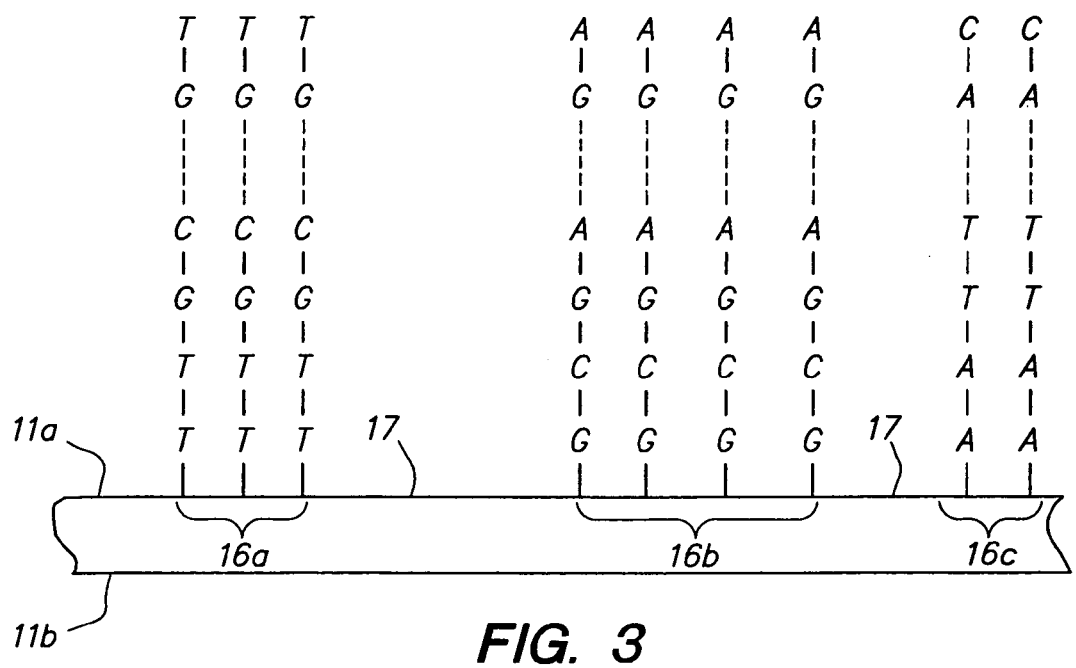
FIG. 3 is an enlarged illustration of a portion of the substrate in FIG. 2.

Referring first to FIGS. 1–3, typically methods and apparatus of the present invention generate or use a contiguous planar substrate 10 carrying multiple arrays 12 disposed successively across a front surface 11a of substrate 10 in a both a first direction 63a and second direction 204a (the second direction 204a being transverse to first direction 63a, that is at some angle to the first direction 63a, most typically orthogonal to first direction 63a). Arrays 12 are separated by inter-array areas 13. A back side 11b of substrate 10 does not carry any arrays 12. All of the arrays 12 on substrate 10 may be the same or any number or all may be different. Each array 12 can be designed for testing against any type of sample, whether a trial sample, reference sample, a combination of them, or a known mixture of polynucleotides (in which latter case the arrays may be composed of features carrying unknown sequences to be evaluated). While ten arrays 12 are shown in FIG. 2 and the different embodiments described below may use substrates with particular numbers of arrays, it will be understood that substrate 10 and the embodiments to be used with it, may use any number of desired arrays 12. Similarly, substrate 10 may be of any shape, and any apparatus used with it adapted accordingly. Depending upon intended use, any or all of arrays 12 may be the same or different from one another and each will contain multiple spots or features 16 of biopolymers in the form of polynucleotides. A typical array may contain from more than ten, more than one hundred, more than one thousand or ten thousand features, or even more than from one hundred thousand features. All of the features 16 may be different, or some or all could be the same. In the case where arrays 12 are formed by the conventional in situ or deposition of previously obtained moieties, as described above, by depositing for each feature a droplet of reagent in each cycle such as by using a pulse jet such as an inkjet type head, interfeature areas 17 (as represented by the distances 17a or 17b) will typically be present which do not carry any polynucleotide. It will be appreciated though, that the interfeature areas 17 could be of various sizes and configurations. It will also be appreciated that there need not be any space separating arrays 12 from one another. Each feature carries a predetermined polynucleotide (which includes the possibility of mixtures of polynucleotides). As per usual, A, C, G, T represent the usual nucleotides. It will be understood that there may be a linker molecule (not shown) of any known types between the front surface 11a and the first nucleotide.

As illustrated in FIG. 2 in particular, each array 12 has multiple sets of neighboring features in the form of multiple rows 15a through 15e (only features of three rows being visible in FIG. 2). All neighboring features within a feature set have the same spacing. It will be understood in this application that "neighboring" feature sets are those which have no other feature set positioned between them. Where a given feature set has closest and further feature sets to which there are no intervening feature sets, only the closest feature sets are considered "neighboring" feature sets. The rows 15a through 15e (which are feature sets) are also arranged successively in the first direction 63a, with each row extending lengthwise in the second direction 204a.

For the purposes of the discussions below, it will be assumed (unless the contrary is indicated) that the array being fabricated is a polynucleotide array formed by the deposition of previously obtained polynucleotides using pulse jet deposition units. However, the applicability of the method to arrays of other polymers or chemical moieties generally, whether formed by multiple cycle in situ methods or deposition of previously obtained moieties, or using other types of dispensers, will be understood from these discussions.

Referring to FIG. 4, operation of a method of the present invention is illustrated to fabricate multiple arrays 12 such as shown in FIGS. 1 and 2. FIG. 4 is a view from above looking down (using the orientation of FIG. 5) toward a head system 210 and substrate 10 (not shown in FIG. 4 for clarity) onto which an array is to be fabricated. Head system 210 has two heads 210a and 210b. In FIG. 4 each head 210a and 210b is illustrated with five parallel rows and two columns (all parallel) of dispensers. However, as described below in connection with FIG. 5, each head may in practice have many more rows and columns although the number of rows and columns have been kept low in FIGS. 4 for the purposes of clarity. Each dispenser is illustrated by its drop dispensing outlet (the drop outlet orifice, for example, in a corresponding pulse jet) represented by a hollow circle in FIG. 4. Deposited droplets are represented by the differently shaded circles (solid black or with a pattern). Since, as described below in connection with FIG. 5, heads 210a and 210b are both mounted to the same head retainer 208, all drop dispensers will be moved in unison by the transport system (see FIG. 5). These drop dispensers are identified as five successive sets in the form of successive rows A, B, C, D, and E in FIG. 4, and four columns 1, 2, 3, and 4. Note that these rows are both successive, and sequential in a direction opposite first direction 63a, in that as head 210 is advanced in first direction 63a, rows E, D, C, B, and A, in that order, pass a given position in relation to substrate 10. In the discussion of FIG. 4 any particular drop dispenser will be referenced by row number followed by column number. For example, drop dispenser A1 refers to the dispenser in row A, column 1, and drop dispenser B2 refers to the drop dispenser in row B, column 2. Drops deposited by a same one of the dispenser rows, have the same shading. Referring particularly to FIG. 4G, nine full arrays each of 4×5 features are fabricated, these arrays being in array rows 14a, 14b, 14c, and twelve partially completed arrays are fabricated in array rows 14d, 14e, 14f, and 14g. Array rows 14a through 14g are both successive, and sequential in that order in first direction 63a, as they are fabricated in that order as head system 210 is advanced in first direction 63a. Similarly, rows 15a through 15e are successive and sequential in the first direction. All arrays are in array columns 9a, 9b, 9c, each array having feature rows 15a through 15e and feature columns 1 through 4.

In the method, all twenty drop dispensers in head system 210 are typically first loaded with different moieties (such as different polynucleotides) although one or more of the dispensers may be loaded with the same moieties. Head system 210 is then advanced in the second direction 204a over the substrate while dispensing drop sets from successive dispenser rows for each array 12, such that each drop set for multiple arrays 12 is deposited by a corresponding dispenser set which earlier deposited at a same feature set position within a previous array. If only one column 9a of multiple arrays 12, for example, was to be fabricated, then the advancing could be essentially continuous in direction 63a. However, since multiple columns 9a, 9b, 9c of arrays 12 are to be fabricated, this advancing is intermittent. In particular, this advancing and dispensing operates as follows. First, while head system 210 remains stationary in a same position in the first direction (that is, while head system 210 does not move in first direction 63a), it is moved in second direction 204a with multiple sets of drops being deposited by dispenser row E. That is, a drop is deposited from each of dispensers 4, 3, 2, and 1 of dispenser set E, in that order, as each of those dispensers passes in turn over the positions for features 4, 3, 2, 1 in row 15a of array column 9a. This is repeated in row 15a of array columns 9b, 9c as head system 210 continues to travel in the second direction 210a with respect to substrate 10. Head system 210 is then returned to the left as viewed in FIG. 4. The result of such a "first pass" of head system 210, is drops deposited at feature locations of a first row 15a for each of three arrays to be formed in a row 14a of arrays (see FIG. 4G). Each part of FIG. 4 shows the results of an additional pass after return of head system 210 in a direction opposite second direction 204a but before further advancement of head system 210 in first direction 63a for the next pass.

Figure 4B:
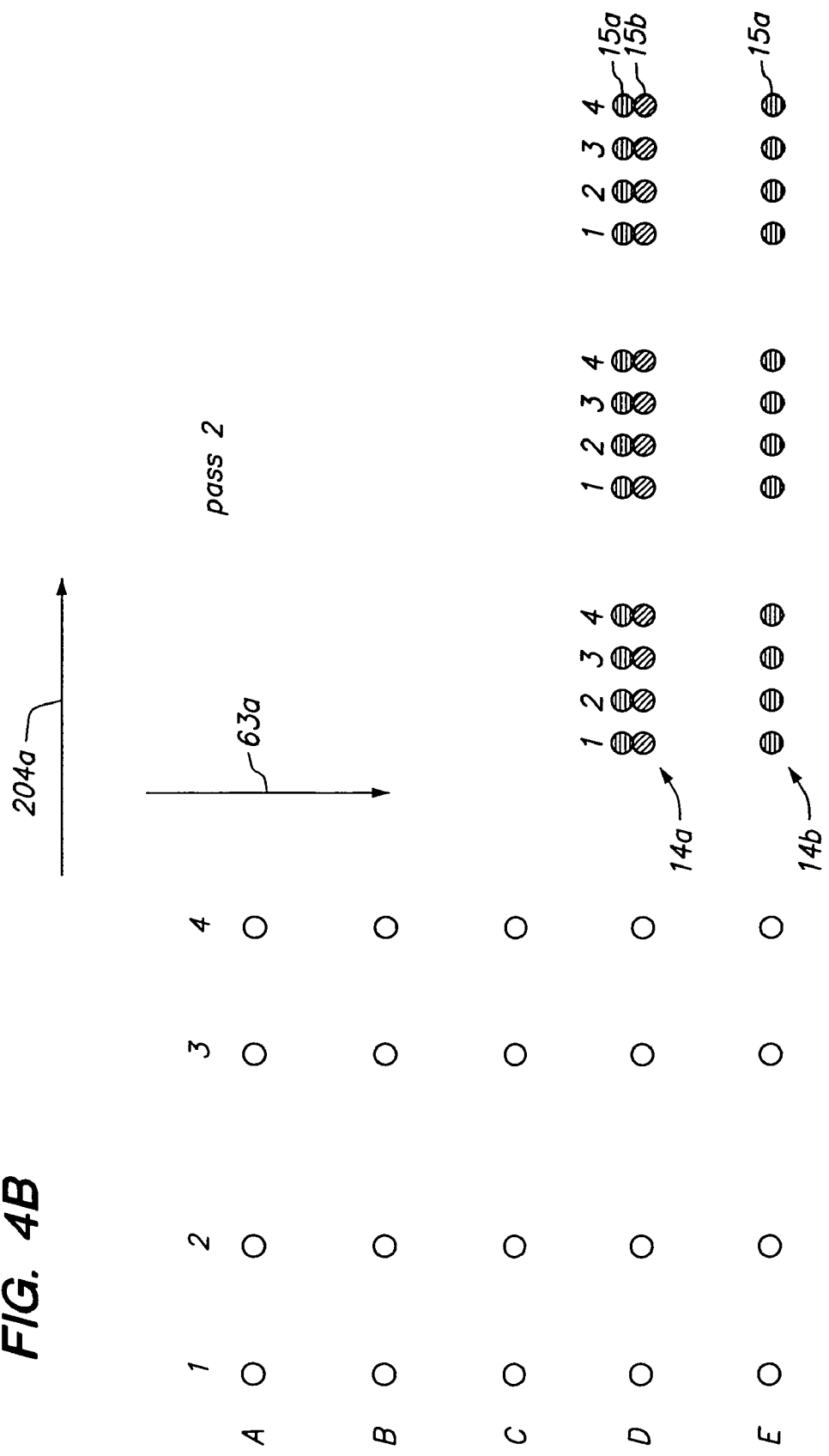
FIG. 4 schematically illustrates operation of an embodiment of the method of the present invention.
Figure 4C:
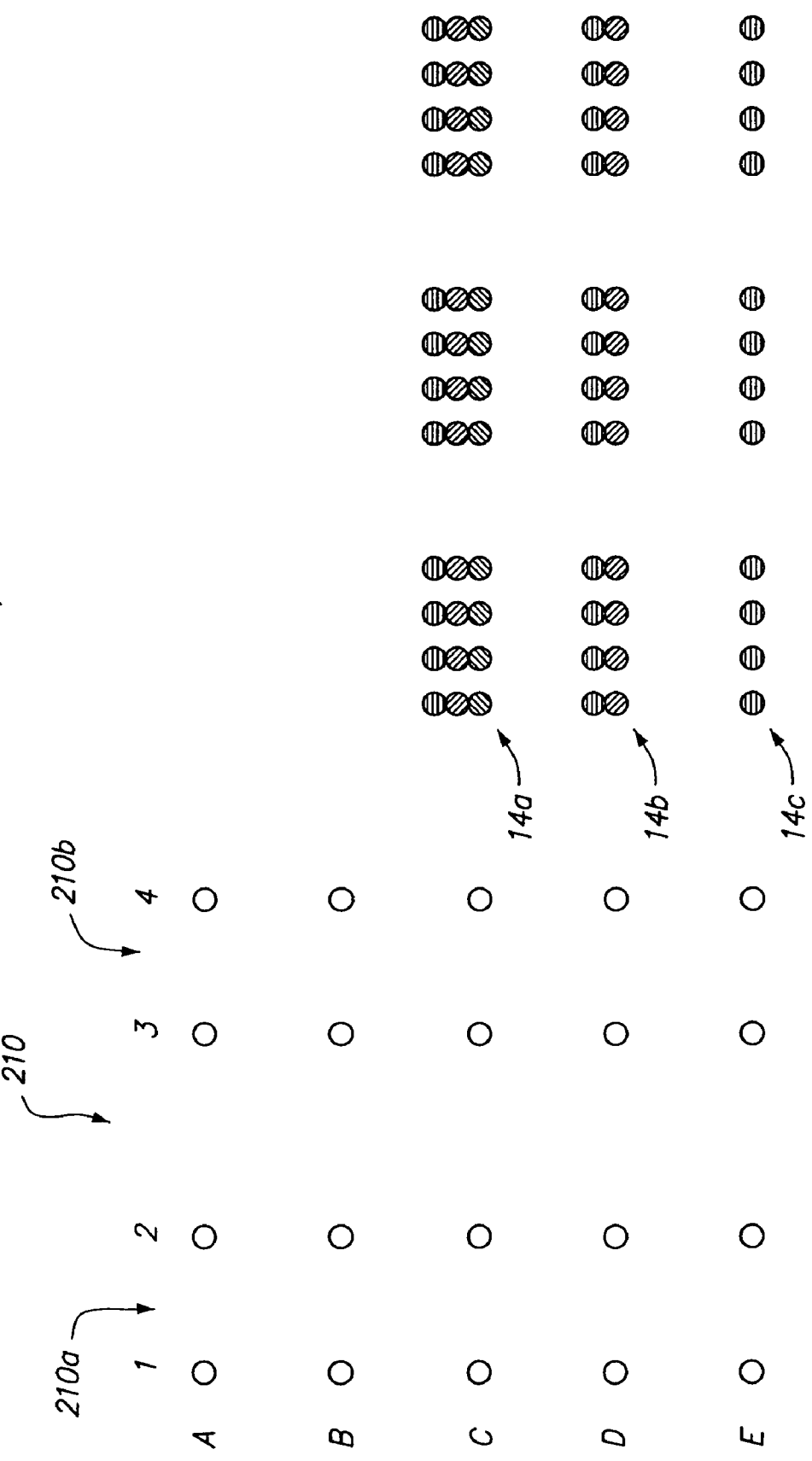
Figure 4E:
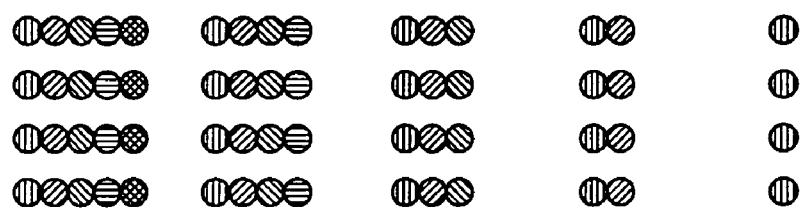
Figure 4E:
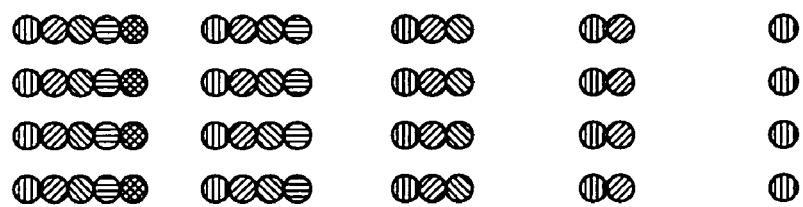
Figure 4E:
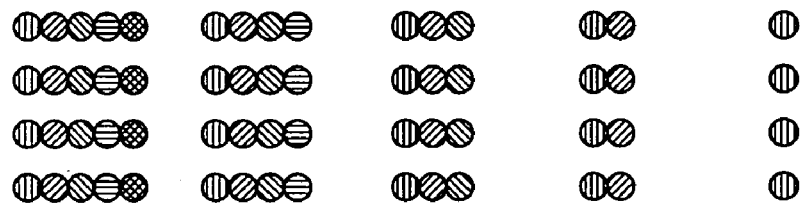
Figure 4F:
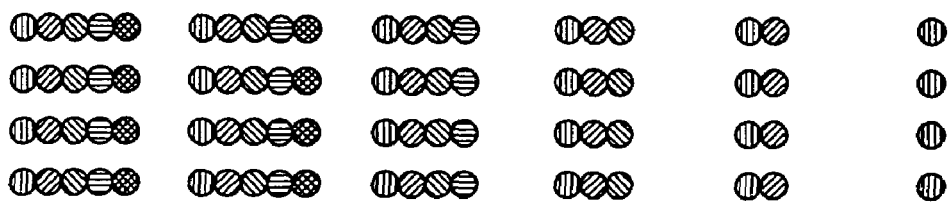
Figure 4F:
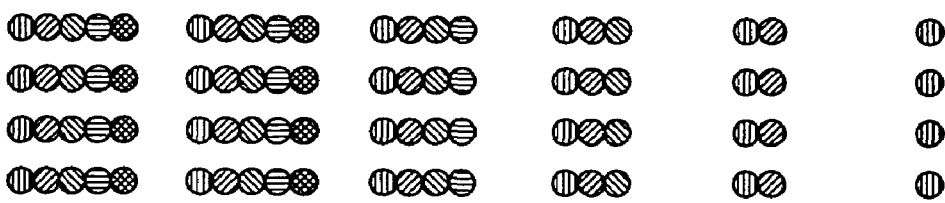
Figure 4F:
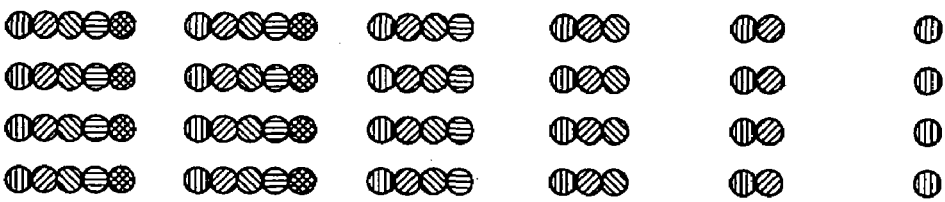
Figure 4G:
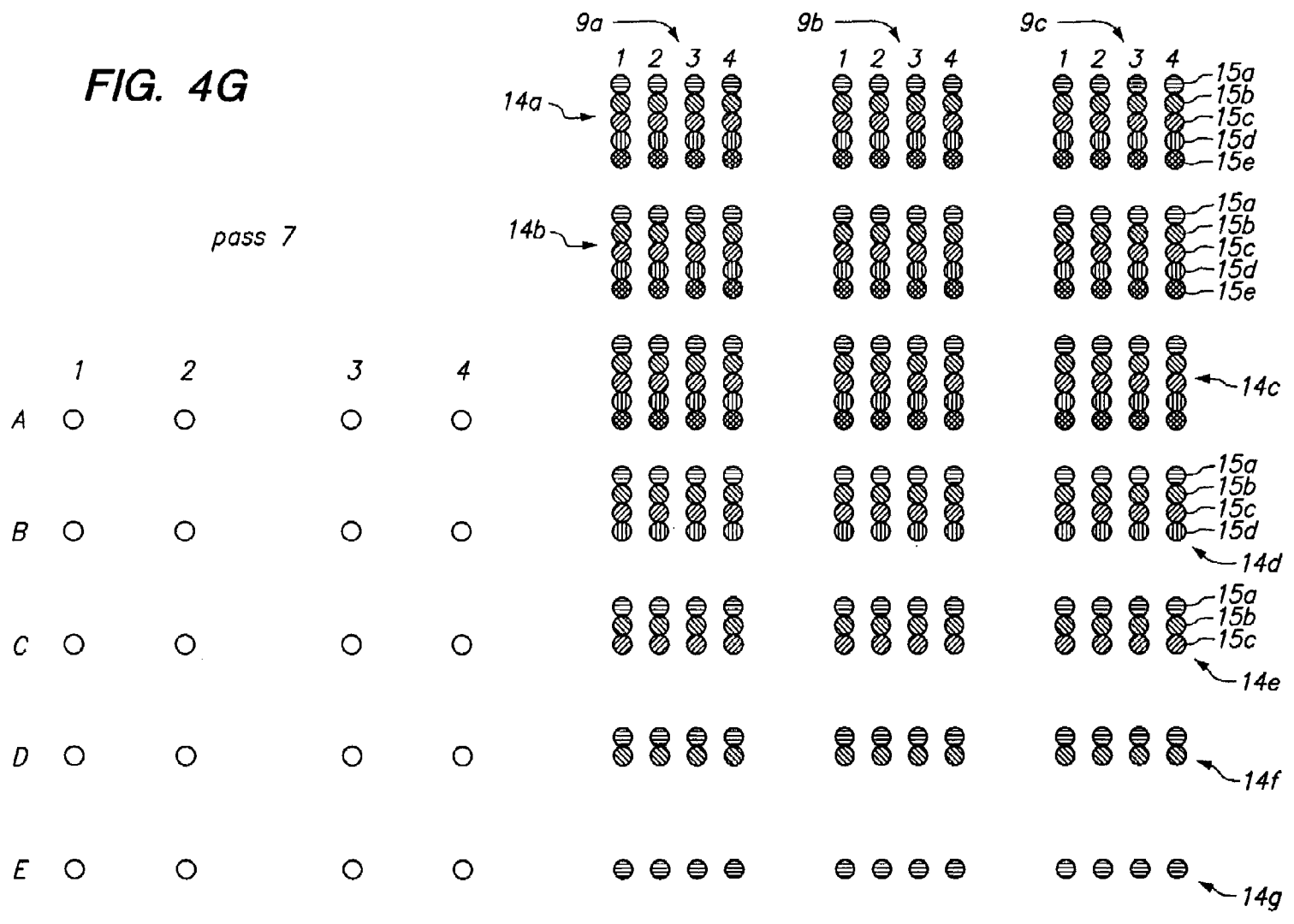

Head system 210 is then advanced in first direction 63a with respect to substrate 10 to a next position, and a second pass of head system 210 over substrate 10 is executed. During this second pass the same pattern of deposition is repeated but with drop sets being deposited from both of dispenser rows D and E. The results of such a second pass will be the additional deposition of drops at feature locations of a second feature row 15b (which is successive to feature row 15a) for each of the three arrays to be formed in row 14a of arrays (deposited by row D of dispensers), and drops deposited at feature locations of a first row 15a for the three arrays to be formed in a row 14b of arrays (deposited by row E of dispensers). A third "pass" of head system 210 is executed as illustrated in FIG. 4C but dispensing drop sets from rows C, D, and E of dispensers. Fourth, fifth, sixth, and seventh passes are illustrated in FIGS. 4D, 4E, 4F, and 4G, respectively. Note that by pass five (FIG. 4E) all dispenser rows A through E are dispensing drop sets. On each following pass, another row of arrays is completed as the top row of nozzles in the printhead fills in the bottom row of the array. Nine completed arrays of twenty features each, can be seen in FIG. 4G. Further passes can be executed as desired and limited only by the size of substrate 10.

The number of passes required to print N rows of complete arrays using head system 210 as illustrated, is N+4. The final arrays are spaced equal to the dispenser nozzle spacing plus one spacing between adjacent features. Alternatively, for subsequent passes in FIGS. 4B through 4G, the head system 210 can be incremented by a spacing equal to that of the nozzle rows and the features printed to the right of (as viewed in FIG. 4) drops deposited from previous passes rather than below. Further, combinations of the foregoing two methods can be used. The method selected depends on the number of fluids to be dispensed and the total number of dispensers available.

Note that during each cycle (or pass) of the steps each of multiple rows of features are deposited by a corresponding dispenser row which deposited at a same feature set position of a previous array during a previous pass. For example, in the third pass (FIG. 4C) the first feature row 15a of array row 14c was deposited by dispenser row E which also deposited at the same feature row position (that is, a first row 15a) of array row 14b previously deposited during the second pass. Similarly, during the third pass the second feature row 15b of array row 14b was deposited by dispenser row D which also deposited at the same feature row position (that is, a second row 15b) of array row 14a previously deposited during the second pass. Also, as can be particularly seen from FIG. 4G, the distance between adjacent feature rows within any of the arrays is less than the distance between adjacent dispenser sets (that is, the rows of dispensed drops are "compressed" relative to the respective dispenser rows). Similarly, columns 1–4 of deposited droplets are spaced closer together than the columns 1–4 of respective dispensers (that is, the dispensed drop columns are "compressed" relative to the respective dispensers). This decrease in deposited drop spacing in any direction of travel of the head system, is readily obtained with pulse jet dispensers by processor 140 correctly timing dispenser actuation as head system 210 moves over the substrate. Such compression allows for arrays with deposited drop spacing as measured in any direction of head travel relative to the substrate, to be independent of the spacing of the respective dispensers which deposited them.

In FIG. 4, head system 210 is not reloaded. However, it will be appreciated that when the present method is used to fabricate arrays using the in situ method as described above (wherein solutions of monomers are dispensed), head system 210 can be reloaded with another set of monomers and the procedure repeated as often as necessary to fabricate the arrays of polymers. It will also be appreciated that arrays with a greater number of features can be obtained. This can be accomplished, for example, by leaving sufficient space between the four by five arrays deposited in FIG. 4 (which can then be regarded as "sub-arrays" of respective larger arrays to be fabricated). Head system 210 can then be reloaded and the procedure repeated depositing further sub-arrays in the space between the sub-arrays deposited in a first round. It will further be appreciated that techniques of this application or the two applications entitled "Array Fabrication" by Peter Webb filed the same date as the present application and both assigned to Agilent Technologies, Inc. Ser. Nos. 09/628,963 and 10/959,639, may be combined as appropriate.

Figure 5:
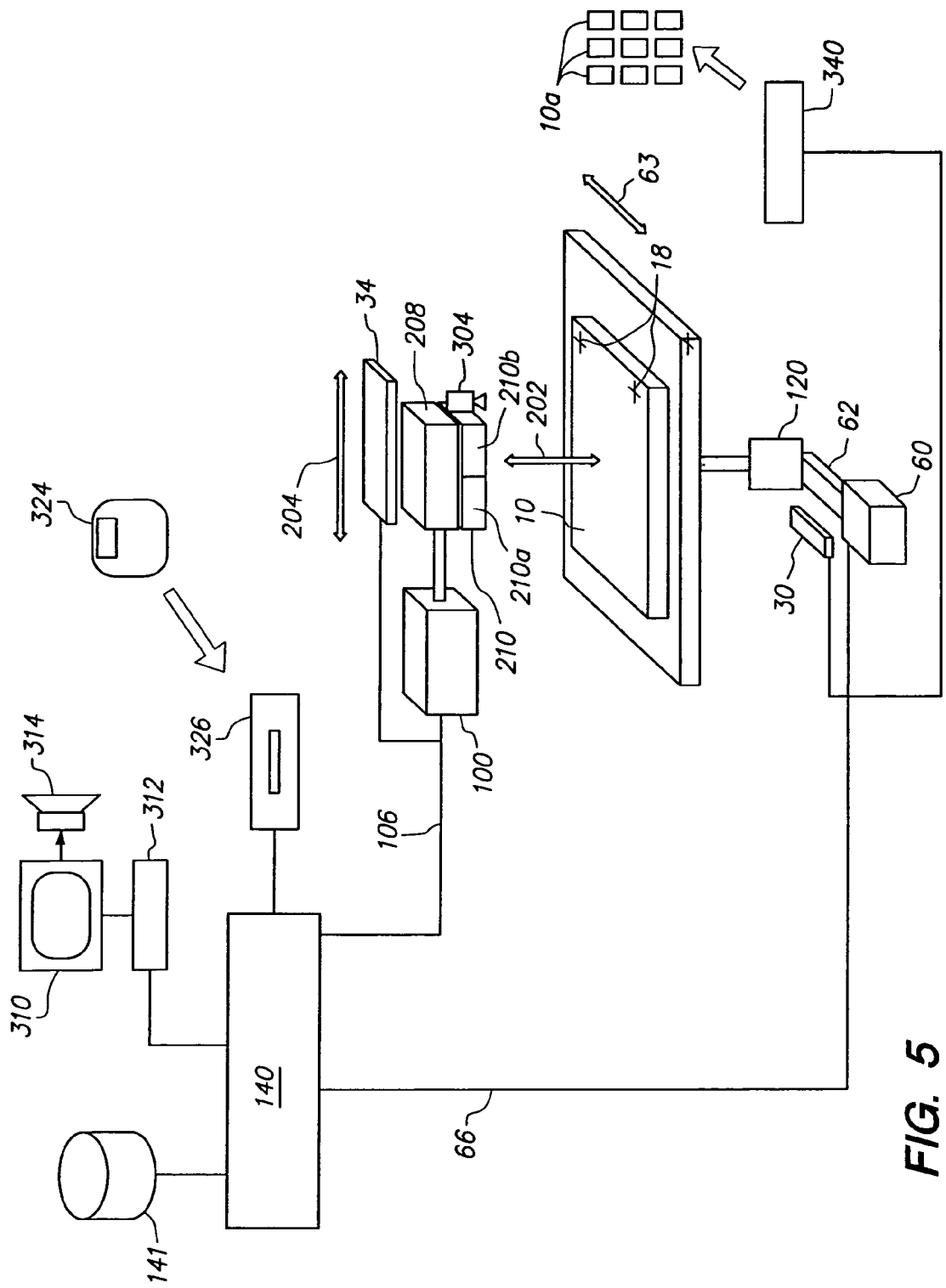
FIG. 5 is an apparatus of the present invention.

Referring to FIG. 5 an apparatus of the present invention is more fully shown, and includes a substrate station 20 on which can be mounted a substrate 10. Pins or similar means (not shown) can be provided on substrate station 20 by which to approximately align substrate 10 to a nominal position thereon. Substrate station 20 can include a vacuum chuck connected to a suitable vacuum source (not shown) to retain a substrate 10 without exerting too much pressure thereon, since substrate 10 is often made of glass.

A dispensing head system 210 is retained by a head retainer 208. Head system 210 can be positioned at any position facing substrate 10 by means of a transport system. The transport system includes a carriage 62 connected to a first transporter 60 controlled by processor 140 through line 66, and a second transporter 100 controlled by processor 140 through line 106. Transporter 60 and carriage 62 are used execute one axis positioning of station 20 (and hence mounted substrate 10) facing the dispensing head system 210, by moving it in the direction of nominal axis 63, while transporter 100 is used to provide adjustment of the position of head retainer 208 in a direction of nominal axis 204 (which includes direction 204a) and hence move the rows of dispensers as described in connection with FIG. 4. In this manner, head system 210 can be scanned line by line, by scanning along a line over substrate 10 in the direction of axis 204 using transporter 100, while line by line movement of substrate 10 in a direction of axis 63 (which includes direction 63a) is provided by transporter 60. Head system 210 may also optionally be moved in a vertical direction 202, by another suitable transporter (not shown). However, it will be appreciated that other scanning configurations could be used. However, it will be appreciated that both transporters 60 and 100, or either one of them, with suitable construction, could be used to perform the foregoing scanning of head system 210 with respect to substrate 10. Thus, when the present application refers to "positioning" one element (such as head system 210) in relation to another element (such as one of the stations 20 or substrate 10) it will be understood that any required moving can be accomplished by moving either element or a combination of both of them. An encoder 30 communicates with processor 140 to provide data on the exact location of substrate station 20 (and hence substrate 10 if positioned correctly on substrate station 20), while encoder 34 provides data on the exact location of holder 208 (and hence head system 210 if positioned correctly on holder 208). Any suitable encoder, such as an optical encoder, may be used which provides data on linear position. Angular positioning of substrate station 20 is provided by a transporter 120, which can rotate substrate station 20 about axis 202 under control of processor 140. Typically, substrate station 20 (and hence a mounted substrate) is rotated by transporter 120 under control of processor 140 in response to an observed angular position of substrate 10 as determined by processor 140 through viewing one or more fiducial marks on substrate 10 (particularly fiducial marks 18) with a camera (not shown). This rotation will continue until substrate 10 has reached a predetermined angular relationship with respect to dispensing head system 210. In the case of a square or rectangular substrate, the mounted substrate 10 will typically be rotated to align one edge (length or width) with the scan direction of head system 210 along axis 204.

Head system 210 may contain one or more (for example, two) heads 210a, 210b mounted on the same head retainer 208. Each such head may be of a type commonly used in an ink jet type of printer and may, for example, have one hundred fifty drop dispensing orifices in each of two parallel rows, six chambers for holding polynucleotide solution communicating with the three hundred orifices, and three hundred ejectors which are positioned in the chambers opposite a corresponding orifice. Each ejector is in the form of an electrical resistor operating as a heating element under control of processor 140 (although piezoelectric elements could be used instead). Each orifice with its associated ejector and portion of the chamber, defines a corresponding pulse jet with the orifice acting as a nozzle. Thus, there are three hundred pulse jets in this configuration, although it will be appreciated that head system 210 could, for example, have more or less pulse jets as desired (for example, at least ten or at least one hundred pulse jets). In this manner, application of a single electric pulse to an ejector causes a droplet to be dispensed from a corresponding orifice. In the foregoing configuration, typically about twenty orifices in each group of six reservoirs (many of the orifices are unused and are plugged with glue), will be dispensing the same fluid. Thus, each "series" in such a configuration has twenty dispensers. Certain elements of each head can be adapted from parts of a commercially available thermal inkjet print head device available from Hewlett-Packard Co. as part no. HP51645A. The foregoing head system 210 and other suitable dispensing head designs are described in more detail in U.S. patent application entitled "A MULTIPLE RESERVOIR INK JET DEVICE FOR THE FABRICATION OF BIOMOLECULAR ARRAYS" Ser. No. 09/150,507 filed Sep. 9, 1998, incorporated herein by reference. However, other head system configurations can be used.

As is well known in the ink jet print art, the amount of fluid that is expelled in a single activation event of a pulse jet, can be controlled by changing one or more of a number of parameters, including the orifice diameter, the orifice length (thickness of the orifice member at the orifice), the size of the deposition chamber, and the size of the heating element, among others. The amount of fluid that is expelled during a single activation event is generally in the range about 0.1 to 1000 pL, usually about 0.5 to 500 pL and more usually about 1.0 to 250 pL. A typical velocity at which the fluid is expelled from the chamber is more than about 1 m/s, usually more than about 10 m/s, and may be as great as about 20 m/s or greater. As will be appreciated, if the orifice is in motion with respect to the receiving surface at the time an ejector is activated, the actual site of deposition of the material will not be the location that is at the moment of activation in a line-of-sight relation to the orifice, but will be a location that is predictable for the given distances and velocities.

The sizes of the features can have widths (that is, diameter, for a round spot) in the range from a minimum of about 10 µm to a maximum of about 1.0 cm. In embodiments where very small spot sizes or feature sizes are desired, material can be deposited according to the invention in small spots whose width is in the range about 1.0 µm to 1.0 mm, usually about 5.0 µm to 500 µm, and more usually about 10 µm to 200 µm. Spot sizes can be adjusted as desired, by using one or a desired number of pulses from a pulse jet to provide the desired final spot size.

Multiple pulse jets of head 210 can be simultaneously loaded through orifices (sometimes referenced as "nozzles") of the pulse jets at a loading station (not shown). The loading station may have multiple receptacles to retain multiple different fluids such that the dispensers can be simultaneously brought into contact with respective receptacles for loading the dispensers with the different fluids. Such a loading station may include a flexible microtitre plate as described in U.S. patent application "Method and Apparatus for Liquid Transfer", Ser. No. 09/183,604. The transport system can move head 210 to such a loading station, as required.

The apparatus optionally may optionally include a sensor in the form of a camera 304, to monitor for errors (such as failure to dispense droplets) by monitoring for drops dispensed onto substrate 10 when required of a dispenser. Camera 304 communicates with processor 140, and should have a resolution that provides a pixel size of about 1 to 100 micrometers and more typically about 4 to 20 micrometers or even 1 to 5 micrometers. Any suitable analog or digital image capture device (including a line by line scanner) can be used for such camera, although if an analog camera is used processor 140 should include a suitable analog/digital converter. A detailed arrangement and use of such a camera to monitor for dispenser errors, is described in U.S. patent application Ser. No. 09/419,447 entitled "Biopolymer Array Inspection" by William D. Fisher. Particular observations techniques are described, for example, in co-pending U.S. patent application Ser. No. 09/302,898 filed Apr. 30, 1999 by Caren et al., assigned to the same assignee as the present application, incorporated herein by reference. Alternatively, the sensor can be a drop detector which detects an electrical charge on a dispensed drop, in accordance with the apparatus and methods described in U.S. Ser. No. 09/558,532 entitled "Array Fabrication with Drop Detection" filed by Christopher A. Schantz et al. Monitoring can occur during formation of an array and the information used during fabrication of the remainder of that array or another array, or test-print patterns can be run before array fabrication.

A display 310, speaker 314, and operator input device 312, are further provided. Operator input device 312 may, for example, be a keyboard, mouse, or the like. Processor 140 has access to a memory 141, and controls print head system 210 (specifically, the activation of the ejectors therein), operation of the transport system, operation of each jet in print head system 210, capture and evaluation of images from the camera 304, and operation display 310 and speaker 314. Memory 141 may be any suitable device in which processor 140 can store and retrieve data, such as magnetic, optical, or solid state storage devices (including magnetic or optical disks or tape or RAM, or any other suitable device, either fixed or portable). Processor 140 may include a general purpose digital microprocessor suitably programmed from a computer readable medium carrying necessary program code, to execute all of the functions required of it as described below. It will be appreciated though, that when a "processor" such as processor 140 is referenced throughout this application, that such includes any hardware and/or software combination which will perform the required functions. Suitable programming can be provided remotely to processor 140, or previously saved in a computer program product such as memory 141 or some other portable or fixed computer readable storage medium using any of those devices mentioned below in connection with memory 141. For example, a magnetic or optical disk 324 may carry the programming, and can be read by disk reader 326. A cutter 340 is provided which under control of processor 140 can separate substrate 10 by cutting it, into multiple equal sized substrate segments 10*a* each carrying at least one array 12.

Operation of the apparatus of FIG. 5 in accordance with a method of the present invention, will now be described. First, it will be assumed that memory 141 holds a target drive pattern. This target drive pattern is the instructions for driving the apparatus components as required to form the target array (which includes target locations and dimension for each spot) on substrate 10 and includes, for example, movement commands to transporters 60 and 100 as well as firing commands for each of the pulse jets in head system 210 co-ordinated with the movement of head system 210 and substrate 10, as well as instructions for which polynucleotide solution (or precursor) is to be loaded in each pulse jet (that is, the "loading pattern"). This target drive pattern is based upon the target array pattern and can have either been input from an appropriate source (such as input device 312, a portable magnetic or optical medium, or from a remote server, any of which communicate with processor 140), or may have been determined by processor 140 based upon an input target array pattern (using any of the appropriate sources previously mentioned) and the previously known nominal operating parameters of the apparatus. Further, it will be assumed that drops of different biomonomer or biopolymer containing fluids (or other fluids) have been placed at respective regions of a loading station (not shown). Operation of the following sequences are controlled by processor 140, following initial operator activation, unless a contrary indication appears.

For any given substrate 10, the operation of the present method is basically follows. A target drive pattern is determined (if not already provided) to obtain multiple target arrays, based on nominal operating parameters and target polynucleotide array pattern. The apparatus is then operated as follows: (a) load head system 210 with a first set of polynucleotide containing solutions or their precursors; (b) dispense droplets from head system 210 onto substrate 10 using multiple passes as described above; and (c) optionally reload head 210 at the loading station and repeat steps (a) and (b) as desired until drops of all required solutions have been dispensed onto substrate 10 so as to form the multiple arrays 12.

A loading sequence for head system 210 is more completely described in co-pending patent applications "FABRICATING BIOPOLYMER ARRAYS", by Caren et al., Ser. No. 09/302,922, and "PREPARATION OF BIOPOLYMER ARRAYS" by A. Schleifer et al., Ser. No. 09/302,899, both filed Apr. 30, 1999 and both assigned to the same assignee as the present application, and the references cited therein, including the possibility of using a flexible microtitre plate as mentioned above. Those references and all other references cited in the present application, are incorporated into this application by reference. Processor 140 can control pressure within head system 210 to load each polynucleotide solution into the chambers in the head by drawing it through the orifices as described in one or more of the foregoing applications.

Substrate 10 is loaded onto substrate station 20 either manually by an operator, or optionally by a suitable automated driver (not shown) controlled, for example, by processor 140.

The deposition sequence is then initiated to deposit the desired arrays of polynucleotide containing fluid droplets on the substrate according to the target pattern to form the arrays each with respective feature locations and dimensions. As already mentioned, in this sequence processor 140 will operate the apparatus according to the target drive pattern, by causing the transport system to position head system 210 facing substrate station 20, and particularly the mounted substrate 10, and with head system 210 at an appropriate distance from substrate 10. Processor 140 then causes the transport system to scan head system 210 across substrate 10 line by line (or in some other desired pattern), while co-ordinating activation of the ejectors in head system 210 so as to dispense droplets, using multiple passes as described above. As already mentioned, if necessary or desired, processor 140 can repeat the loading and multiple passes one or more times until head system 210 has dispensed droplets to obtain the target arrays 12 on substrate 10. The number of spots in any one array 12 can, for example, be at least ten, at least one hundred, at least one thousand, or even at least one hundred thousand.

At this point the droplet dispensing sequence is complete. Substrate 10 can then be sent to cutter 340 and cut into separate segments 10*a*, each carrying at least one array 12.

When a user receives an array made by an apparatus or method of the present invention, it will typically be exposed to a sample and the array interrogated following exposure. Interrogation is usually accomplished by a suitable scanner which can read the location and intensity of fluorescence at each feature of an array following exposure to a fluorescently labeled sample (such as a polynucleotide containing sample). For example, such a scanner may be similar to the GENEARRAY scanner available from Hewlett-Packard, Palo Alto, Calif. Results from the interrogation can be processed such as by rejecting a reading for a feature which is below a predetermined threshold and/or forming conclusions based on the pattern read from the array (such as whether or not a particular target sequence may have been present in the sample). The results of the interrogation or processing can be forwarded (such as by communication) to a remote location if desired, for further use.

The present methods and apparatus may be used to deposit biopolymers or other chemical moieties on surfaces of any of a variety of different substrates, including both flexible and rigid substrates. Preferred materials provide physical support for the deposited material and endure the conditions of the deposition process and of any subsequent treatment or handling or processing that may be encountered in the use of the particular array. The array substrate may take any of a variety of configurations ranging from simple to complex. Thus, the substrate could have generally planar form, as for example a slide or plate configuration, such as a rectangular or square or disc. In many embodiments, the substrate will be shaped generally as a rectangular solid, having a length in the range about 4 mm to 1 m, usually about 4 mm to 600 mm, more usually about 4 mm to 400 mm; a width in the range about 4 mm to 1 m, usually about 4 mm to 500 mm and more usually about 4 mm to 400 mm; and a thickness in the range about 0.01 mm to 5.0 mm, usually from about 0.1 mm to 2 mm and more usually from about 0.2 to 1 mm. However, larger substrates can be used, particularly when such are cut after fabrication into smaller size substrates carrying a smaller total number of arrays 12.

In the present invention, any of a variety of geometries of arrays on a substrate 10 may be fabricated other than the rectilinear rows and columns of arrays 12 of FIG. 1. For example, arrays 12 can be arranged in a sequence of curvilinear rows across the substrate surface (for example, a sequence of concentric circles or semi-circles of spots), and the like. Similarly, the pattern of features 16 may be varied from the rectilinear rows and columns of spots in FIG. 2 to include, for example, a sequence of curvilinear rows across the substrate surface (for example, a sequence of concentric circles or semi-circles of spots), and the like. In such cases, the arrangement of dispensers in head system 210 may be altered accordingly. The configuration of the arrays and their features may be selected according to manufacturing, handling, and use considerations.

The substrates may be fabricated from any of a variety of materials. In certain embodiments, such as for example where production of binding pair arrays for use in research and related applications is desired, the materials from which the substrate may be fabricated should ideally exhibit a low level of non-specific binding during hybridization events. In many situations, it will also be preferable to employ a material that is transparent to visible and/or UV light. For flexible substrates, materials of interest include: nylon, both modified and unmodified, nitrocellulose, polypropylene, and the like, where a nylon membrane, as well as derivatives thereof, may be particularly useful in this embodiment. For rigid substrates, specific materials of interest include: glass; plastics (for example, polytetrafluoroethylene, polypropylene, polystyrene, polycarbonate, and blends thereof, and the like); metals (for example, gold, platinum, and the like).

The substrate surface onto which the polynucleotide compositions or other moieties is deposited may be smooth or substantially planar, or have irregularities, such as depressions or elevations. The surface may be modified with one or more different layers of compounds that serve to modify the properties of the surface in a desirable manner. Such modification layers, when present, will generally range in thickness from a monomolecular thickness to about 1 mm, usually from a monomolecular thickness to about 0.1 mm and more usually from a monomolecular thickness to about 0.001 mm. Modification layers of interest include: inorganic and organic layers such as metals, metal oxides, polymers, small organic molecules and the like. Polymeric layers of interest include layers of: peptides, proteins, polynucleic acids or mimetics thereof (for example, peptide nucleic acids and the like); polysaccharides, phospholipids, polyurethanes, polyesters, polycarbonates, polyureas, polyamides, polyethyleneamines, polyarylene sulfides, polysiloxanes, polyimides, polyacetates, and the like, where the polymers may be hetero- or homopolymeric, and may or may not have separate functional moieties attached thereto (for example, conjugated).

Various further modifications to the particular embodiments described above are, of course, possible. Accordingly, the present invention is not limited to the particular embodiments described in detail above.

What is claimed is:

1. An apparatus for fabricating multiple arrays of biopolymers arranged successively in a first direction on a substrate and each having multiple feature sets arranged successively in the first direction within the array, the apparatus comprising:

(a) a head system with multiple successive sets of dispensers wherein the head system is loaded with biopolymers or biomonomers;
   (b) a transport system to advance the head system in the first direction with respect to a substrate; and
   (c) a processor communicating with the head system and transport system to advance the head system in the first direction over the substrate while dispensing drop sets for each array, from dispenser sets in an order the reverse of that from which the dispenser sets pass over a given location on the substrate as the head system advances in the first direction, with each dispenser set depositing a drop set at a distance ahead of a drop set deposited by a preceding dispenser set which is less than the distance to the successive drop dispenser set which deposits the next drop set, so as to form the arrays.

2. An apparatus according to claim 1 wherein the distance between adjacent feature sets within the arrays is less than the distance between adjacent dispenser sets.

3. An apparatus according to claim 1 wherein the advancing and dispensing comprises:

(a) while the head system is in one position in the first direction, depositing drop sets from different dispenser sets for feature sets of different positions within multiple arrays;
   (b) advancing the head system in the first direction to a next position; and
   (c) repeating steps (a) and (b) for successive feature sets within the arrays using for each of those feature sets during a cycle, a corresponding dispenser set which deposited at a same feature set position of a previous array in step (a) during a previous cycle.

4. An apparatus according to claim 1 wherein the feature sets are rows of features, the sets of dispensers are rows of dispensers, and the dispensed drop sets are rows of drops.

5. An apparatus according to claim 1 wherein the dispensers are pulse jets.

6. An apparatus according to claim 1 wherein the head system is loaded with biomonomers.

7. An apparatus according to claim 1 wherein the head system is loaded with polynucleotides, peptides, nucleotides, or amino acids.

8. An apparatus according to claim 1 wherein the head system is loaded with polynucleotides or peptides.

9. An apparatus according to claim 8 wherein the head system is loaded with polynucleotides.

10. An apparatus according to claim 1 wherein the head system is loaded with nucleotides or amino acids.

11. An apparatus according to claim 10 wherein the head system is loaded with nucleotides.

12. A computer program product comprising a computer readable storage medium having a computer program stored thereon for use with an apparatus for fabricating multiple arrays arranged successively in a first direction on a substrate and each having multiple feature sets arranged successively in the first direction within the array, which apparatus has:

(i) a head system with multiple successive sets of dispensers wherein the head system is loaded with biopolymers or biomonomers;
   (ii) a transport system to advance the head system in a first direction with respect to a substrate; and
   (iii) a processor communicating with the head system and transport system;
   the computer program product, when loaded into the processor, performs the steps of:

advancing the head system in the first direction over the substrate while dispensing drop sets for each array from dispenser sets in an order the reverse of that from which the dispenser sets pass over a given location on the substrate as the head system advances in the first direction, with each dispenser set depositing a drop set at a distance ahead of a drop set deposited by a preceding dispenser set which is less than the distance to the successive drop dispenser set which deposits the next drop set, so as to form the arrays.

13. A computer program product according to claim 12 wherein the distance between adjacent feature sets within the arrays is less than the distance between adjacent dispenser sets.

14. A computer program product according to claim 12 wherein the advancing and dispensing comprises:

(a) while the head system is in one position in the first direction, depositing drop sets from different dispenser sets for feature sets of different positions within multiple arrays;

(b) advancing the head system in the first direction to a next position; and (c) repeating steps (a) and (b) for successive feature sets within the arrays using for each of those feature sets during a cycle, a corresponding dispenser set which deposited at a same feature set position of a previous array in step (a) during a previous cycle.

* * * * *